(12) United States Patent
de la Torre et al.

(10) Patent No.: US 7,559,937 B2
(45) Date of Patent: Jul. 14, 2009

(54) SURGICAL FASTENER APPARATUS AND REINFORCING MATERIAL

(75) Inventors: Roger A. de la Torre, Wentzville, MO (US); Matthew P. LaConte, Maryland Heights, MO (US)

(73) Assignee: TowerTech Research Group, Wentzville, MO (US)

( * ) Notice: Subject to any disclaimer, the term of this patent is extended or adjusted under 35 U.S.C. 154(b) by 626 days.

(21) Appl. No.: 11/199,733

(22) Filed: Aug. 9, 2005

(65) Prior Publication Data

US 2007/0034669 A1  Feb. 15, 2007

(51) Int. Cl.
*A61B 17/10* (2006.01)
*A61B 17/04* (2006.01)
(52) U.S. Cl. .................. 606/142; 606/151; 606/219; 606/75; 227/176.1; 227/179.1; 227/180.1; 227/178.1; 227/19

(58) Field of Classification Search .............. 606/151, 606/219, 75, 142; 227/176.1, 179.1, 180.1, 227/178.1, 175.1, 19
See application file for complete search history.

(56) References Cited

U.S. PATENT DOCUMENTS

| 5,397,324 | A | * | 3/1995 | Carroll et al. ............... 606/139 |
| 5,415,334 | A | | 5/1995 | Williamson, IV et al. |
| 5,752,965 | A | | 5/1998 | Francis et al. |
| 6,656,193 | B2 | * | 12/2003 | Grant et al. ................. 606/151 |
| 6,706,048 | B2 | | 3/2004 | de la Pena et al. |

\* cited by examiner

*Primary Examiner*—(Jackie) Tan-Uyen T Ho
*Assistant Examiner*—Christina Lauer
(74) *Attorney, Agent, or Firm*—Thompson Coburn LLP; Joseph M. Rolnicki

(57) ABSTRACT

A surgical fastener apparatus is provided with a reinforcement material holder, where the holder positions a sheet of reinforcement material adjacent body tissue that is sutured by a plurality of surgical staples dispensed by the apparatus.

11 Claims, 7 Drawing Sheets

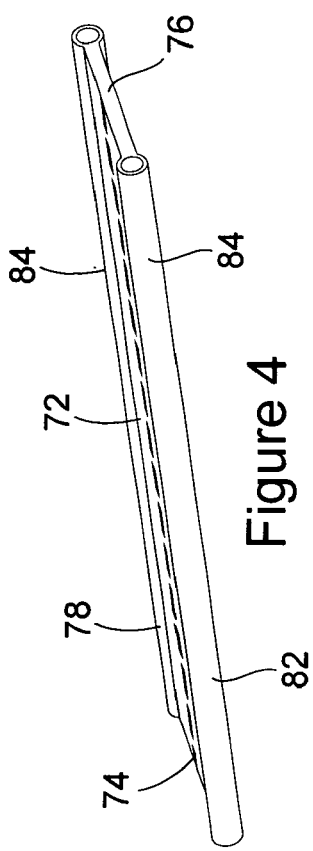
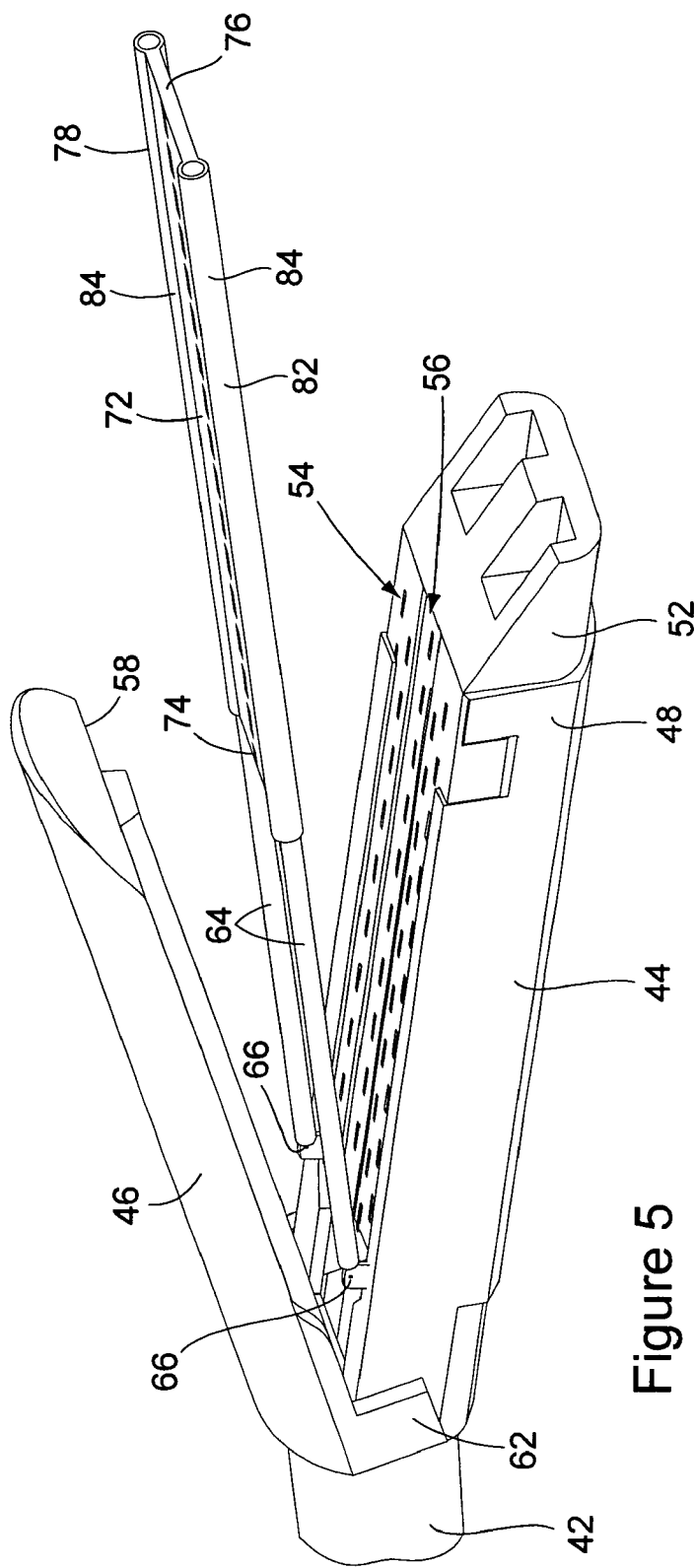

SURGICAL FASTENER APPARATUS AND REINFORCING MATERIAL

BACKGROUND OF THE INVENTION (1) Field of the Invention

The present invention pertains to a surgical fastener apparatus that dispenses a fastener reinforcing material, and the method of using the apparatus. In particular, the present invention pertains to a surgical stapler having a reinforcement material holder, where the holder positions a sheet of reinforcement material adjacent body tissue that is sutured by a plurality of surgical staples dispensed by the apparatus.

(2) Description of the Related Art

A variety of different types of surgical staplers have been developed to assist surgeons by reducing the time required for placing a line of sutures in body tissue. Surgical staplers have been designed for use in open incision surgery, as well as in laparoscopic surgery. Examples of these staplers are shown in the Williamson, et al. U.S. Pat. No. 5,415,334, and the Francis U.S. Pat. No. 5,752,965, et al. both of which are incorporated herein by reference.

Surgical staplers used in both open incision surgery and in laparoscopic surgery have several common features. The staplers typically include a pair of opposed, movable jaws. One of the jaws functions as a staple dispensing member, and the opposite jaw functions as a staple receiving and staple altering member.

The staple dispensing member supports a plurality of surgical staples that are arranged in at least two rows that extend along the length of the dispensing member. When operated by the surgeon, the staple dispensing member ejects the staples into body tissue to be sutured, thereby forming parallel lines of sutures through the body tissue.

The staple receiving member has a plurality of anvil surface areas that are positioned opposite the staples on the staple dispensing member. The anvil surfaces are adapted to engage the ends of staples ejected by the staple dispensing member, and to alter or bend the staple ends, thereby securing a staple sutures in body tissue.

In the typical surgical stapler, the staple dispensing member and the staple receiving member are held together by a mechanical connection that allows relative movement between the two members, for example a pivot connection. This connection enables the staple dispensing member and the staple receiving member to move toward each other when the surgical stapler is used, closing a portion of body tissue to receive the surgical staplers between the dispensing member and the receiving member. As the dispensing member and the receiving member come together on opposite sides of the body tissue, the surgical staples are ejected from the dispensing member, through the body tissue, and the ends of the staples engage against the anvil surfaces of the receiving member which alter or deform the staple ends and secure the staple sutures in the body tissue.

The typical surgical stapler also includes a cutter that cuts along a line through the body tissue that has been sutured by the surgical stapler. The cutter is positioned so that the cut line through the body tissue has pluralities of staple sutures formed along opposite sides of the cut line. In this manner, the surgical stapler provides a cut through body tissue, while also suturing the body tissue along opposite sides of the cut line.

The use of surgical staplers in securing together body tissue has been found to be disadvantaged in that the punctures formed through the body tissue as the staples are inserted can become a starting point for a tear developing in the stapled body tissue. As a result, the typical surgical stapler has been modified to include some type of reinforcement material that is also stapled to the body tissue as the surgical staples are dispensed from the stapler.

In one example of reinforcement material that is used with a surgical stapler, the reinforcement material is designed as a tape with an adhesive on one side. The adhesive adheres the reinforcement material to the surgical stapler. As surgical staples are dispensed from the stapler, the staples peel away the reinforcement material from the surgical stapler and secure the reinforcement material along the line of sutures in the body tissue.

In other examples of the reinforcement material, a separate adhesive is used to adhere the reinforcement material to the surgical stapler. The reinforcement material is adhered to the stapler in a position where a staple being dispensed will pass through the reinforcement material and peel the material from the stapler. The staples secure the material to the sutured body tissue, and thereby the material reinforces the body tissue against tearing at the punctures formed by the surgical stapler.

However, the modification of surgical staplers to include a reinforcing material adhered to the surgical stapler has detracted from the primary purpose of the stapler, i.e., to facilitate the placement of a plurality of sutures in body tissue in a quick and reliable manner. The need to adhere the reinforcement material to the surgical stapler adds an additional preparatory step to using the stapler, and detracts from the ease of using the stapler. Furthermore, the adhesive holding the material to the stapler could be difficult to peel away from the stapler, making it difficult to dispense the staples.

What is needed to overcome this disadvantage associated with the prior art surgical staplers is an apparatus and method of removably holding a reinforcement material adjacent the staple dispensing member of a surgical stapler, where the reinforcement material is easily positioned on the stapler, and is easily removed from the stapler.

SUMMARY OF THE INVENTION

Although the apparatus and method of the invention are described herein as being employed on a particular type of surgical stapler, the concept of the invention could be used with other types of surgical instruments that dispense other types of sutures into body tissue. Thus, the concept of the invention may be employed with other types of instruments that dispense surgical fasteners, and should not be interpreted as being limited to use with surgical staplers of the type described and shown herein.

The present invention overcomes disadvantages associated with prior art surgical staplers discussed earlier by providing a surgical stapler that has a reinforcement material holder that enables a sheet of reinforcement material to be removably held by the surgical stapler. The present invention also provides a modified sheet of reinforcement material that is removably held by the surgical stapler of the invention. The present invention also provides a method of using a reinforcement material with a surgical stapler, where the reinforcement material is removably attached to the surgical stapler without the need for adhesives, and where the reinforcement material is easily separated from the surgical stapler in use of the stapler.

The invention may be provided on a surgical stapler when the stapler is manufactured, or may be employed in modifying many of the surgical staplers currently used. The surgical stapler of the invention differs from prior art surgical staplers in that it comprises a reinforcement material holder that removably holds a sheet of reinforcement material between the staple dispensing member and the staple receiving member (or anvil side) of the surgical stapler. The reinforcement material holder can be provided on the staple dispensing member to hold the reinforcement material against the dispensing member, or could be provided on the staple receiving member (or anvil side) to hold the reinforcement material against the receiving member. In a further invariant embodiment of the invention, the surgical stapler could be provided with a pair of reinforcement material holders, one on the staple dispensing member and one on the staple receiving member. The holder and material sheet of the invention may also be employed on surgical staplers that are used in open incision surgery, and in endoscopic and laparoscopic surgery.

The surgical stapler, or other surgical fastener dispensing apparatus of the invention comprises a surgical fastener dispensing member and a surgical fastener receiving member that are positioned opposite each other. The fastener dispensing member and the fastener receiving member are connected together by a connection that enables the members to move selectively toward and away from each other on operation of a mechanical actuator, as is typical in the construction of such devices. The fastener dispensing member and the fastener receiving member are mounted to a handle that is easily gripped by the surgeon in manipulating the apparatus. The handle could be provided adjacent the dispensing member and the fastener receiving member, or could be at the opposite end of an elongate flexible applicator for use of the surgical stapler in endoscopic and laparoscopic surgery. The actuator of the apparatus is positioned on the handle in easy reach of the surgeon. Operation of the actuator selectively moves the fastener dispensing member toward the fastener receiving member, and discharges the fasteners from the dispensing member to the receiving member where the fasteners are bent or otherwise altered to secure body tissue in the fasteners.

The apparatus of the invention differs from prior art surgical fastener dispensers in that it is provided with a reinforcement material holder. In the preferred embodiment, the reinforcement material holder is comprised of a pair of elongate arms that are connected to the apparatus at the opposite sides of either of the fastener dispensing member and the fastener receiving member. The pair of arms extend along the lengths of the fastener dispensing member and the fastener receiving member. The arms are movable relative to both the fastener dispensing member and the fastener receiving member to facilitate the positioning of reinforcing material on the pair of arms.

The reinforcing material is formed from a sheet of any type of material that is used in reinforcing sutures in body tissue. In the preferred embodiment, the reinforcing material has a rectangular configuration.

The sheet of reinforcing material is formed with a pair of tubes or sleeves that extend along opposite side edges of the material sheet. The tubes or sleeves are dimensioned to slide easily over the pair of arms of the reinforcing material holder. In positioning the pair of arms through the tubes or sleeves, the sheet of reinforcing material is removably attached to the reinforcing material holder, and is removably attached to the surgical fastener dispensing apparatus of the invention.

In use of the apparatus of the invention, the sheet of reinforcing material is first removably attached to the pair of arms of the reinforcing material holder. The apparatus of the invention is then basically operated in a conventional manner.

With the apparatus opened and the fastener dispensing member being spaced from the fastener receiving member, the reinforcing material sheet removably mounted on the material holder is positioned adjacent one of the dispensing member or receiving member. The apparatus is then manipulated by the surgeon to position the body tissue to be sutured between the dispensing member and receiving member. The apparatus is then operated to cause the dispensing member to move toward the receiving member, closing the body tissue to be sutured between the dispensing member and the receiving member with the reinforcing material sheet held against the body tissue.

The surgeon then actuates the apparatus to cause the fasteners to be dispensed from the fastener dispensing member. In the conventional manner, the fasteners are driven through the body tissue from the fastener dispensing member to the fastener receiving member, where the ends of the fasteners are altered or bent over to securely hold the fasteners in the body tissue. At the same time, the ends of the fasteners are driven through the reinforcing material sheet adjacent the body tissue. Thus, the reinforcing material sheet is also sutured to the body tissue.

Subsequently, or in sequence with the dispensing of the surgical fasteners through the reinforcing material and the body tissue, a cutter on the apparatus advances through the sutured body tissue and the sheet of reinforcing material. The cutter cuts through the body tissue and the reinforcing material along a line of cut, where at least one row of fasteners securing the body tissue and securing the reinforcing material is positioned on each side of the line of cut. When the cutting procedure is completed, the apparatus is opened and removed from the body tissue.

With the apparatus removed from the body tissue, the body tissue has been cut through with a line of surgical fasteners secured to the body tissue on opposite sides of the line of cut. In addition, portions of the reinforcing material that were cut apart at the same time the tissue was cut are secured to the body tissue by the same surgical fasteners securing the body tissue.

Thus, the sheet of reinforcing material and the reinforcing material holder of the invention provide an economical and easily used modification of the standard surgical fastener apparatus that reinforces the line of sutures produced by the modified apparatus.

In a variant embodiment of the apparatus of the invention, the apparatus is provided with a pair of reinforcement material holders. Each reinforcement material holder is comprised of a pair of elongate arms. One pair of arms is connected at the opposite sides of the fastener dispensing member, and the other pair of arms is connected at the opposite sides of the fastener receiving member.

A sheet of the reinforcing material is removably attached to each of the reinforcing material holders. One sheet of the reinforcing material is held adjacent the fastener dispensing member, and the other sheet of the reinforcing material is held adjacent the fastener receiving member. This further embodiment of the apparatus of the invention is used in substantially the same manner as the first described embodiment.

BRIEF DESCRIPTION OF THE DRAWINGS

Further features of the invention are set forth in the following detailed description of the preferred embodiment of the invention, and in the drawing figures wherein:

FIG. 4 is a perspective view of a sheet of reinforcing material constructed in accordance with the invention;

FIG. 5 is a view similar to FIG. 3, but showing the sheet of reinforcing material of the invention being removably attached to the apparatus of the invention;

DETAILED DESCRIPTION OF THE PREFERRED EMBODIMENT

Figure 1:
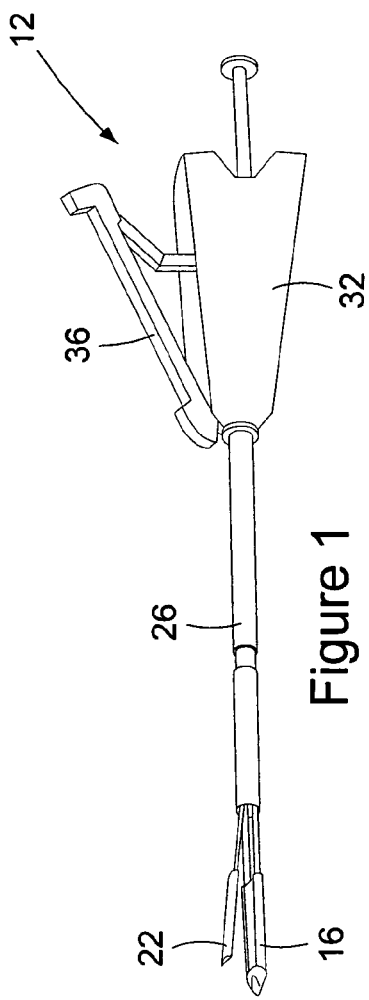
FIG. 1 is a schematic representation of one type of surgical fastener apparatus that could be modified by the apparatus of the invention.
Figure 2:
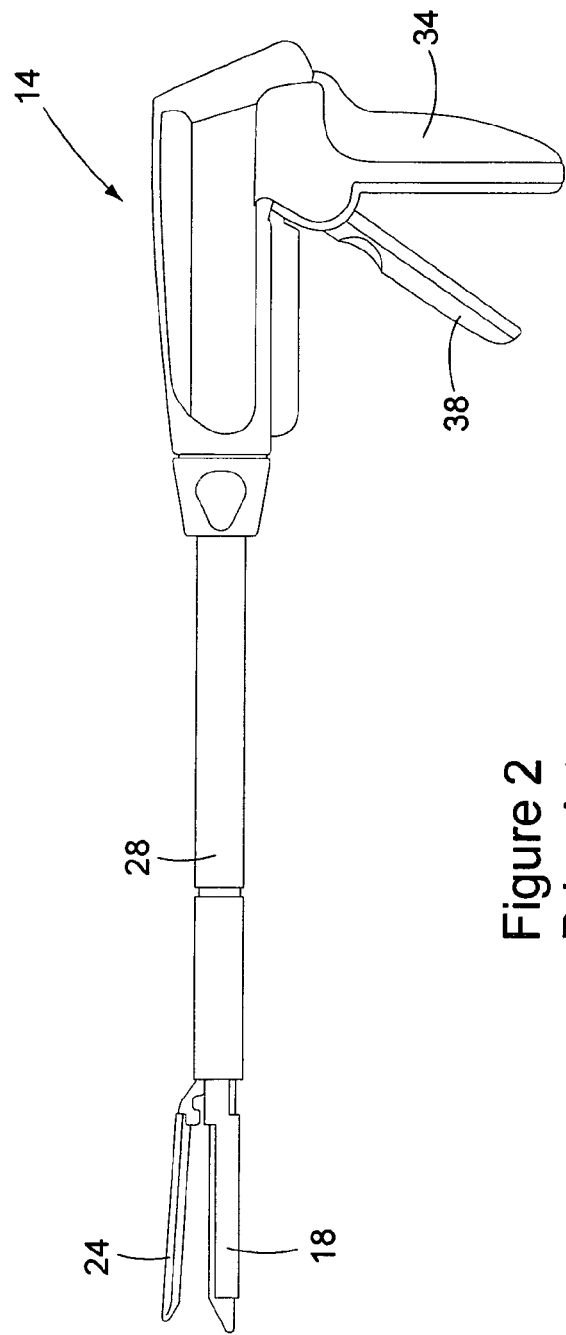
FIG. 2 is a schematic representation of another type of surgical fastener apparatus that could be modified by the apparatus of the invention.

FIGS. 1 and 2 show schematic representations of two examples of prior art surgical stapler apparatus 12, 14 that can be modified with the invention. Although the apparatus examples shown in FIGS. 1 and 2 are described herein as being surgical staplers, it should be understood that the invention may be employed in modifying other types of apparatus that dispense surgical fasteners in suturing body tissue. The following description is not intended to limit the use of the invention with surgical fastener apparatus that only dispense staples.

The examples of the surgical stapler apparatus 12, 14 shown in FIGS. 1 and 2, are well known in the art. Therefore, the apparatus are described only generally herein. Each apparatus has the basic construction of a staple dispensing member 16, 18 and a staple receiving member 22, 24 mounted on a rod portion 26, 28 of the apparatus. The rod portion 26, 28 extends from a handle 32, 24 of the apparatus. Each handle 32, 34 is provided with a trigger mechanism 36, 38 that is manipulated by the surgeon to operate the dispensing of staples from the apparatus.

In the typical operation of the apparatus 12, 14 shown in FIGS. 1 and 2, with the staple dispensing members 16, 18 and the staple receiving members 22, 24 in their opened positions shown, the body tissue (not shown) to be sutured is inserted in the spacing between the two members. With the body tissue so positioned, the surgeon then actuates the apparatus trigger mechanism 36, 38 which causes the dispensing members 16, 18 and the receiving members 22, 24 to move together, closing the tissue between the members. The apparatus is then operated to dispense staples through the body tissue to the staple receiving members 22, 24 where the ends of the staples are bent inwardly, or otherwise altered to complete the suturing of the body tissue by the apparatus.

The present invention modifies apparatus such as that shown in FIGS. 1 and 2 by providing a reinforcement material holder on the apparatus, and a sheet of reinforcement material that is removably attached to the holder. The manner in which the reinforcement material sheet is held to the material holder enables the sheet to be easily mounted on the holder prior to use of the apparatus, and then enables the material sheet to be easily removed from the holder after the use of the apparatus.

Figure 3:
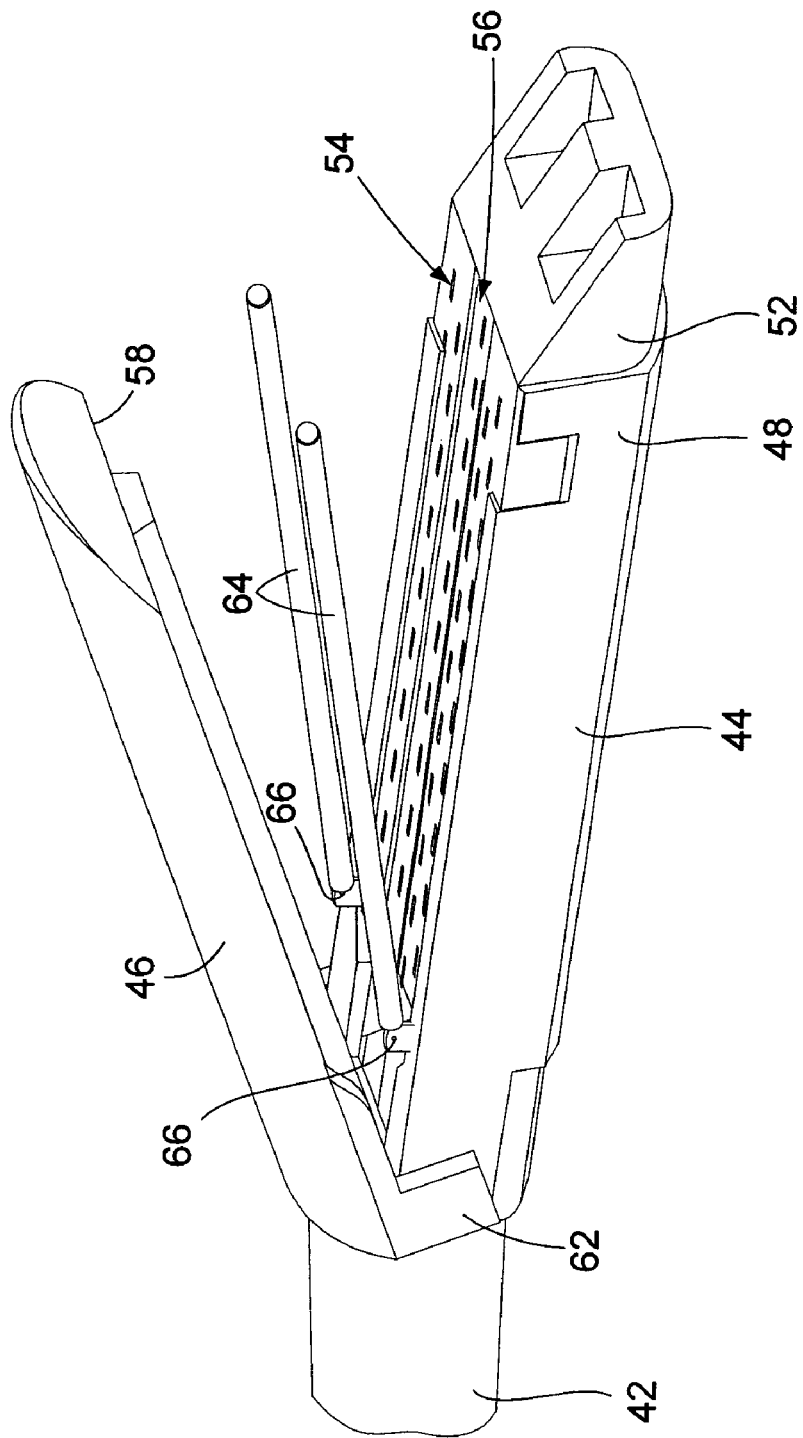
FIG. 3 is a schematic representation of a surgical fastener apparatus modified with the apparatus of the invention.

FIG. 3 shows the distal end portion 42 of a surgical stapler apparatus that has been modified by the invention. Because various types of surgical stapler apparatus may be modified with the invention, only the distal end portion 42 of the apparatus on which the invention is mounted is shown in the drawing figures. The distal end portion 42 of the apparatus shown in the drawing figures could be a portion of a manual actuator of the apparatus. Alternatively, the portion 42 of the apparatus could be the end of an elongate, flexible applicator for use of the apparatus in endoscopic and laparoscopic surgery.

The apparatus of the invention 42 comprises a surgical fastener dispensing member 44 and a surgical fastener receiving member 46 that are of conventional design. Because these two components of the invention are typically found in many of the prior art surgical stapler apparatus, they are only described generally herein.

The surgical fastener dispensing member 44 includes a housing section 48 that projects from the apparatus distal end 42. The housing section 48 has a generally U-shaped cross-section.

A surgical fastener or surgical staple cartridge 52 is received in the housing section 48. The cartridge 52 is removably mounted in the housing section 48 and is easily snapped into the housing section and removed from the housing section. The staple cartridge 52 contains a plurality of surgical staples that can be selectively dispensed from the cartridge 52 through a plurality of staple openings 54 in the cartridge. The staples are selectively dispensed or ejected from the cartridge openings 54 on operation of the apparatus by the surgeon, as is conventional. A slot 56 extends through the length of the cartridge 52. The slot 56 accommodates the cutter of the apparatus that moves through the slot to cut through body tissue that has been sutured by the apparatus, as in conventional.

The surgical fastener receiving member 46 is positioned directly opposite the surgical fastener dispensing member 44, and directly opposite the staple openings 54 of the staple cartridge 52. As is conventional, a surface 58 of the receiving member 46 that opposes the staple cartridge 52 is provided with a plurality of anvil surface areas that are directly opposite the cartridge staple openings 54. The staples that are dispensed or ejected from the staple cartridge openings 54 engage against the anvil surface areas of the receiving member surface 58, and the ends of the staples are altered or bent by the anvil areas of the surface 58, thereby suturing tissue positioned between the dispensing member 44 and the receiving member 46.

The fastener dispensing member 44 and fastener receiving member 46 are connected together by a connection 62 that enables the members to move selectively toward and away from each other on operation of the apparatus. In the preferred embodiment, the connection 62 is a pivoting connection that enables the receiving member 46 to pivot toward and away from the dispensing member 44. The movement of the receiving member 46 about the pivot connection 62 is controlled by the surgeon on actuation of the apparatus trigger actuator, as is conventional.

The reinforcement material holder of the invention is mounted on the apparatus between the surgical fastener dispensing member 44 and the surgical fastener receiving member 46. In the preferred embodiment of the holder, the holder is comprised of a pair of elongate arms or rods 64 that are connected to the apparatus. As shown in FIG. 3, each of the rods 64 is connected to the apparatus by a pivot connection 66 of the rod to the dispensing member housing section 48. The pivot connection 66 enables the rods 64 to move relative to both the dispensing member 44 and the receiving member 46. Each of the rods 64 has a length that extends across the length of the staple cartridge 52 installed on the apparatus. The pivot connection 66 of the rod 64 positions the rods along the opposite sides of the staple cartridge 52. The rods 64 are shown as being separate from each other in FIG. 3. In variant embodiments of the invention, the pair of rods 64 could be interconnected so that both rods pivot together about their pivot connections 66 to the apparatus.

FIG. 4 shows the reinforcing material sheet 72 of the invention. The reinforcing material sheet 72 is formed of any type of material that is used in reinforcing sutures in body tissue. Furthermore, the reinforcing material sheet 72 could be manufactured of any type of material that is biocompatible and will not produce a toxic, injurious, or an otherwise adverse response when left in body tissue. In the preferred embodiment of the reinforcing material sheet 72 shown in FIG. 4, the sheet has a rectangular configuration. The sheet 72 has a length dimension that extends between opposite end edges 74, 76 of the sheet. The sheet 72 also has a width dimension that extends between opposite side edges 78, 82 of the sheet. Within the sheet periphery defined by the end edges 74, 76 and the side edges 78, 82, the sheet 72 is basically one layer of the reinforcement material.

A pair of tubes 84 are formed in the material of the sheet 72. The tubes 84 extend along the entire length of the sheet 72 at the sheet side edges 78, 82. The tubes 84 are dimensioned to slide easily over the pair of material holder arms or rods 64 of the reinforcing material holder. There is sufficient friction engagement between the tubes 84 and the rods 64 to hold the tubes 84 and the reinforcing material sheet 72 stationary on the rods 64. However, the friction engagement force is not sufficient to restrict the easy removal of the tubes 84 and the sheet 72 from the rods 64. Thus, positioning the pair of arms or rods 64 through the reinforcing material sheet tubes 84 removably attaches the reinforcing material sheet 72 on the reinforcing material holder, and removably attaches the sheet 72 to the apparatus distal end 42.

In variant embodiments of the invention, an equivalent means of removably attaching the sheet 72 to the reinforcing material holder could be employed. For example, instead of a pair of rods 64, the reinforcing material holder could be provided with pairs of channels having opposing slots along their lengths. The sheet would be provided with opposite side edges having seams that are received in the channel slots, with the channel slots releasably holding the sheet extending between the two channels.

In use of the apparatus of the invention shown in FIG. 3, the sheet of reinforcing material 72 shown in FIG. 4 is first removably attached to the pair of arms 64 of the reinforcing material holder. As shown in FIG. 5, the sheet 72 is attached to the apparatus by inserting the elongate arms 64 of the material holder into the openings at the ends of the tubes 84 on the sheet 72. The arms 64 are inserted through the tubes 84, positioning the sheet 72 between the pair of arms as shown in FIG. 6.

Figure 6:
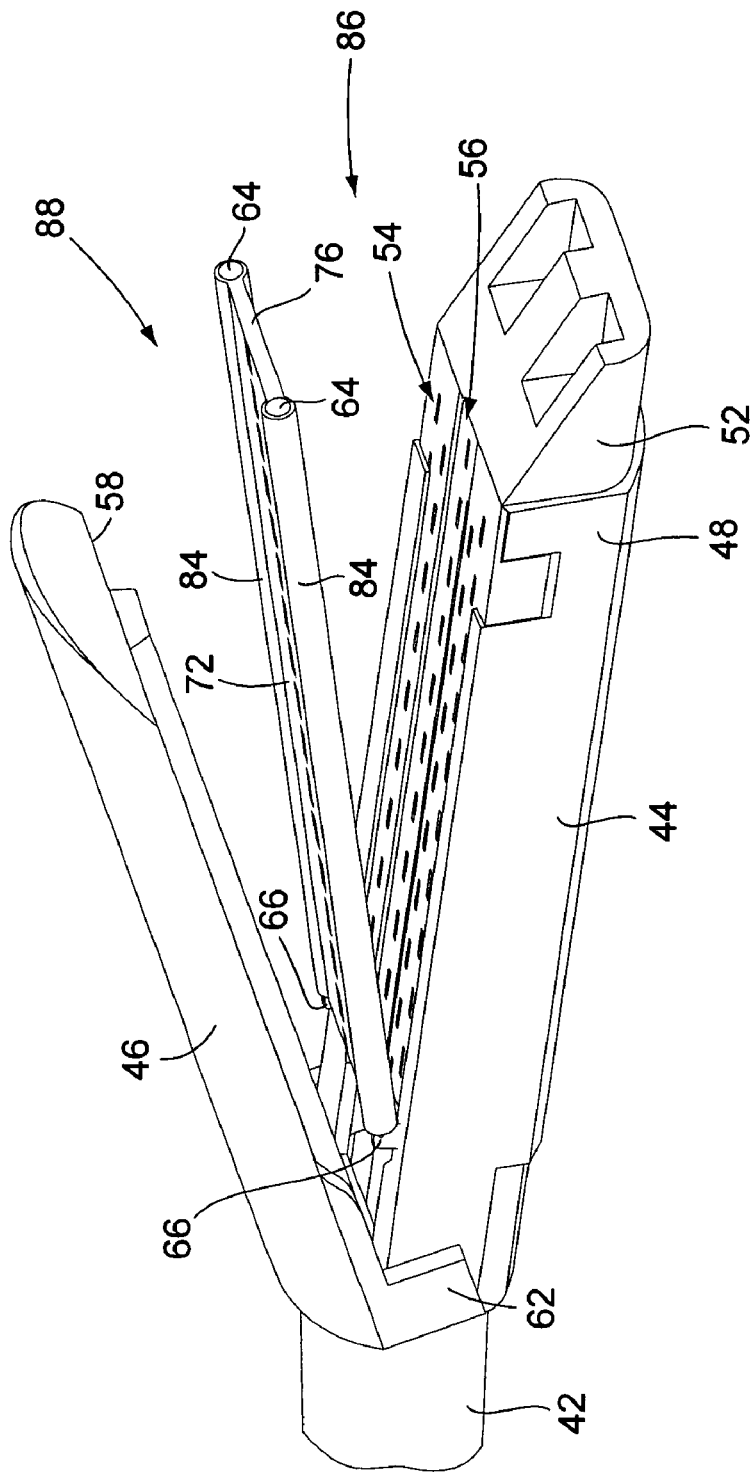
FIG. 6 is a view similar to FIG. 5, but showing the sheet of reinforcing material removably attached to the apparatus, and the apparatus being ready for use in dispensing surgical fasteners through body tissue.

In FIG. 6 that apparatus of the invention is ready for use. The pair of arms 64 of the material holder removably hold the sheet taut between the arms 64 and across all of the plurality of fastener holes 54 of the staple cartridge 52. With the sheet 72 removably mounted to the reinforcing material holder arms 64, the apparatus of the invention is then basically operated in a conventional manner.

With the apparatus opened as shown in FIG. 6, the reinforcing material sheet 72 removably mounted on the material holder arms 64 is positioned adjacent one of the fastener dispensing member 44 or the fastener receiving member 46. The apparatus is then manipulated by the surgeon to position the body tissue to be sutured into the spacing 86 between the dispensing member 44 and the removably held sheet 72, or in the spacing 88 between the removably held sheet 72 and the receiving member 46.

Figure 7:
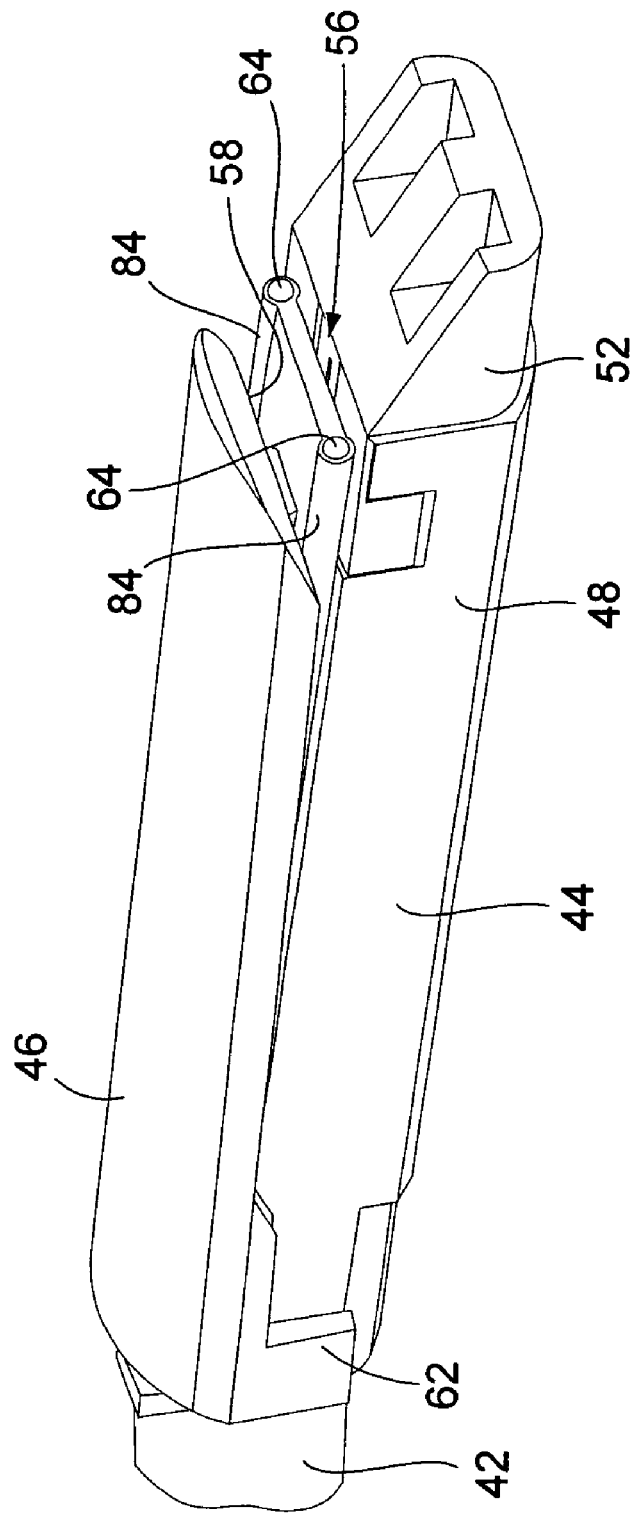
FIG. 7 shows the relative positions of the fastener dispenser, the fastener receiver, and the reinforcing material holder of the apparatus when the apparatus is used in dispensing surgical fasteners.

The apparatus is then operated to cause the dispensing member 44 to move toward the receiving member 46, closing the body tissue to be sutured between the dispensing member and the receiving member with the reinforcing material sheet 72 held against the body tissue. The relative positioning of the dispensing member 44, the receiving member 46, and the removably held sheet 72 is shown in FIG. 7.

The surgeon then actuates the apparatus to cause the fasteners to be dispensed from the fastener dispensing member 44. In the conventional manner, the fasteners are driven through the body tissue from the fastener dispensing member 44 to the fastener receiving member 46, where the ends of the fasteners are altered or bent over to securely hold the fasteners in the body tissue. At the same time, the ends of the fasteners are driven through the reinforcing material sheet 72 held adjacent the body tissue. Thus, the reinforcing material sheet 72 is also sutured to the body tissue.

Subsequently, or in sequence with the dispensing of the surgical fasteners through the reinforcing material sheet and the body tissue, a cutter on the apparatus 42 advances through the sutured body tissue and through the reinforcing material sheet 72. The cutter cuts through the body tissue and the sheet 72 along a line of cut where at least one row of the fasteners securing the body tissue and securing the reinforcing material sheet is positioned on each side of the line of cut. When the cutting procedure is completed, the apparatus is opened and removed from the body tissue. As the apparatus is removed, the material holder arms 64 are withdrawn from the tubes 84 of the cut sheet.

With the apparatus removed from the body tissue, the body tissue has been cut through with a line of surgical fasteners secured to the body tissue on each side of the cut. In addition, portions of the reinforcing material sheet 72 that were cut apart at the same time the tissue was cut are secured to the body tissue by the same surgical fasteners securing the body tissue.

Figure 8:
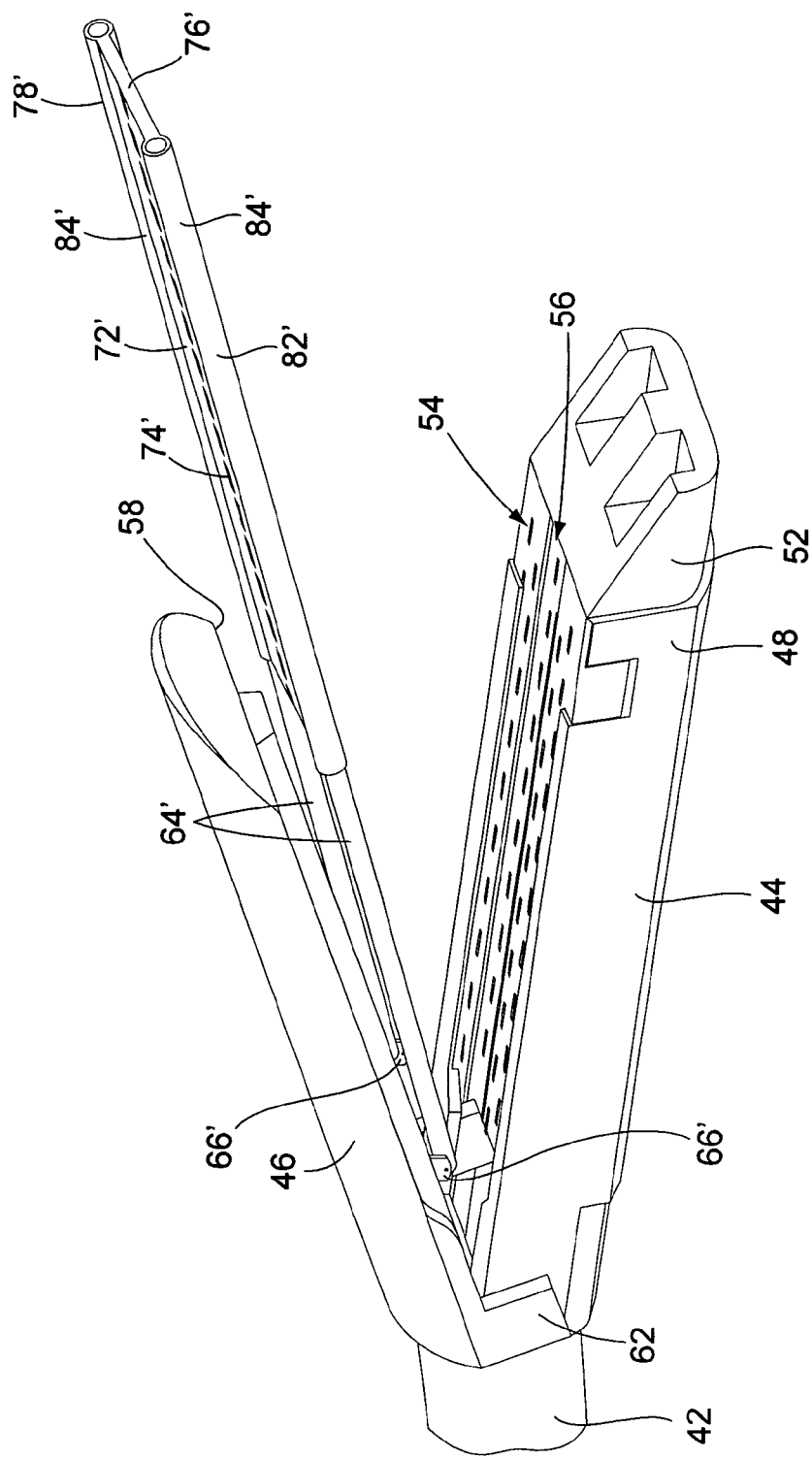
FIG. 8 is a view similar to FIG. 6, but showing a further embodiment of the apparatus; and, FIG. 9 is a view similar to FIG. 6, but showing a still further embodiment of the apparatus.
Figure 9:
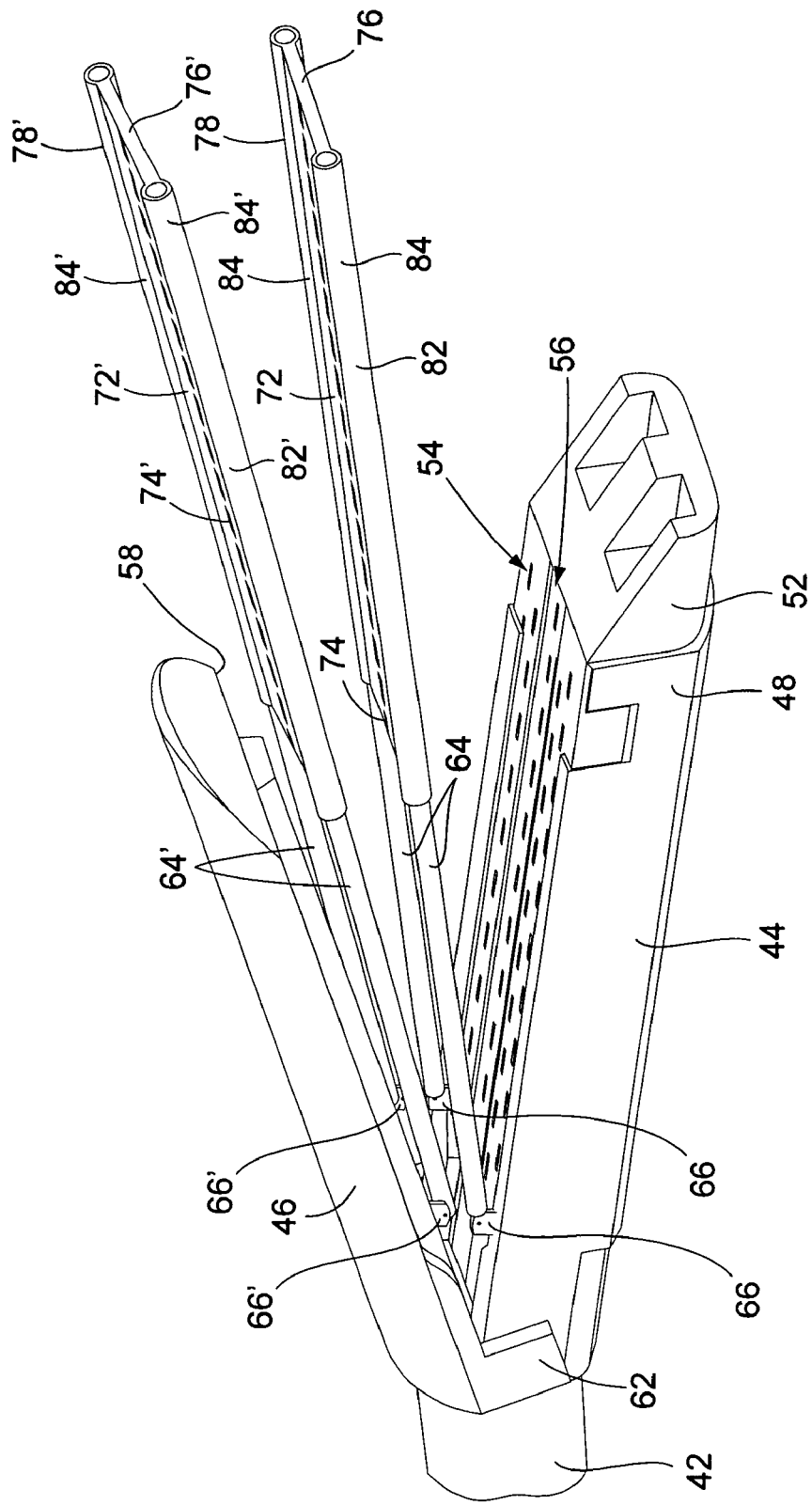

FIGS. 8 and 9 show variant embodiments of the apparatus. These variant embodiments are substantially the same in construction as the previously described embodiment of the apparatus, and therefore the same reference numbers used in describing the first embodiment of the apparatus are also used to label the same component parts shown in FIGS. 8 and 9. The only difference in the embodiments of FIGS. 8 and 9 from the previously described embodiment is in the positioning of the reinforcement material holder, and in the number of reinforcement material holders.

The apparatus of the invention shown in FIG. 8 also comprises a reinforcement material holder mounted on the apparatus between the surgical fastener dispenser member 44 and the surgical fastener receiving member 46. In the embodiment of FIG. 8 however, each of the material holder rods 64' is connected to the apparatus by a pivot connection 66' of the rod to the receiving member housing section 46. This is the only difference in the construction of the embodiment of FIG. 8 from the previously described embodiment. The use of the embodiment of FIG. 8 is the same as that as the previously described embodiment.

FIG. 9 shows a pair of reinforcement material holders mounted on the apparatus between the surgical fastener dispensing member 44 and the surgical fastener receiving member 46. The apparatus of the invention shown in FIG. 9 is basically a combination of the two previously described embodiments of the apparatus. The use of the apparatus of FIG. 9 is substantially the same as that of the first described apparatus, except that the body tissue to be sutured together by the apparatus is positioned between the two reinforcement material holders prior to dispensing of the fasteners.

Although the apparatus and method of the invention have been described above by reference to particular embodiments, it should be understood that modifications and variations could be made to the subject matter of the invention without departing from the intended scope of the following claims.

The invention claimed is:

1. A surgical fastener dispensing apparatus comprising:
   a surgical fastener dispensing member on the apparatus that is operative to dispense at least one surgical fastener;
   a surgical fastener receiving member on the apparatus that is positioned opposite the surgical fastener dispensing member and is operative to receive a surgical fastener dispensed from the surgical fastener dispensing member and to alter the surgical fastener received;
   a reinforcement material holder on the apparatus that is positioned between the surgical fastener dispensing member and the surgical fastener receiving member;
   reinforcement material that is removably mounted on the reinforcement material holder and is positioned between the surgical fastener dispensing member and the surgical fastener receiving member;
   the reinforcement material holder having a pair of arms that are positioned at opposite sides of the surgical fastener receiving member for removably holding the reinforcement material on the pair of arms extending across the surgical fastener receiving member;
   the reinforcement material having opposite side edges;
   the pair of arms being removably attachable to the opposite side edges of the reinforcement material;
   the pair of arms being a pair of elongate, narrow rods with one end of each rod being connected to the apparatus by a pivot connection for movement of each rod relative to the apparatus; and,
   the reinforcement material having a pair of openings that receive the pair of rods inserted into the openings in removably holding the reinforcement material on the pair of arms.

2. The apparatus of claim 1, further comprising:
   the surgical fastener dispensing member having a dispensing surface with a plurality of fastener holes containing a plurality of surgical fasteners;
   the surgical fastener receiving member having a receiving surface with a plurality of fastener contact areas that alter the surgical fasteners received by the surgical fastener receiving member; and,
   the reinforcement material holder holding the reinforcement material extending across the plurality of holes and across the plurality of fastener contact areas.

3. The apparatus of claim 2, further comprising:
   a cutter that is movable across the surgical fastener receiving member and is positioned to cut through the reinforcement material removably mounted on the reinforcement material holder.

4. The apparatus of claim 1, further comprising:
   a cutter that is movable across the surgical fastener receiving member and is positioned to cut through the reinforcement material removably mounted on the reinforcement material holder.

5. A surgical fastener dispensing apparatus comprising:
   a surgical fastener dispensing member on the apparatus that is operative to dispense at least one surgical fastener;
   a surgical fastener receiving member on the apparatus that is positioned opposite the surgical fastener dispensing member and is operative to receive a surgical fastener dispensed from the surgical fastener dispensing member and to alter the surgical fastener received;
   a reinforcement material holder on the apparatus that is positioned between the surgical fastener dispensing member and the surgical fastener receiving member;
   reinforcement material that is removably mounted on the reinforcement material holder and is positioned between the surgical fastener dispensing member and the surgical fastener receiving member;
   the reinforcement material holder having a pair of arms that are positioned at opposite sides of the surgical fastener receiving member for removably holding the reinforcement material on the pair of arms extending across the surgical fastener receiving member;
   the reinforcement material having opposite side edges;
   the pair of arms being removably attachable to the opposite side edges of the reinforcement material;
   the pair of arms being a pair of elongate, narrow rods;
   the opposite side edges of the reinforcement material having a pair of openings that receive the pair of rods inserted into the openings in removably holding the reinforcement material on the pair of arms; and
   the reinforcement material having a pair of tubes with the pair of openings being to the pair of tubes.

6. The apparatus of claim 1, further comprising:
   the reinforcement material holder being permanently attached to the apparatus by a pivot connection and being movable to pivot with the reinforcement material relative to the surgical fastener dispensing member and relative to the surgical fastener receiving member.

7. A reinforcement for a surgical fastener dispensing apparatus having a surgical fastener dispensing member and a surgical fastener receiving member positioned on opposite sides of a reinforcement material holder, the reinforcement comprising:
   a sheet of reinforcement material having a length between opposite end edges of the sheet and a width between opposite side edges of the sheet, the opposite side edges of the sheet being adapted for removable attachment to the reinforcement material holder of the surgical fastener dispensing apparatus;
   the sheet of reinforcement material having a pair of tubes dimensioned to receive a pair of arms of the reinforcement material holder in removably attaching the sheet to the reinforcement material holder.

8. The reinforcement of claim 7, further comprising:
   the length and width of the sheet of reinforcement material being dimensioned to cover over a plurality of fastener holes in the surgical fastener dispensing member.

9. The reinforcement of claim 7, further comprising:
   the sheet of reinforcement material having a pair of openings dimensioned to receive a pair of arms of the reinforcement material holder in removably attaching the sheet to the reinforcement material holder.

10. The reinforcement of claim 7, further comprising:
    the pair of tubes extending along the opposite side edges of the sheet.

11. The reinforcement of claim 7, further comprising:
    the pair of tubes being parallel.

* * * * *